United States Patent
Iyer et al.

(10) Patent No.: US 8,285,379 B2
(45) Date of Patent: Oct. 9, 2012

(54) ELECTRICAL INTERCONNECTION STRUCTURES AND METHOD

(75) Inventors: Rajesh V. Iyer, Eden Prairie, MN (US); William J. Taylor, Anoka, MN (US); Joseph F. Lessar, Coon Rapids, MN (US); Mark D. Breyen, Champlin, MN (US); Daniel J. Koch, Lakeville, MN (US)

(73) Assignee: Medtronic, Inc., Minneapolis, MN (US)

( * ) Notice: Subject to any disclaimer, the term of this patent is extended or adjusted under 35 U.S.C. 154(b) by 1073 days.

(21) Appl. No.: 11/343,107

(22) Filed: Jan. 30, 2006

(65) Prior Publication Data

US 2007/0179555 A1    Aug. 2, 2007

(51) Int. Cl.
*A61N 1/00*    (2006.01)
*H01G 4/35*    (2006.01)
(52) U.S. Cl. .................... 607/36; 607/37; 361/302
(58) Field of Classification Search ............... 607/36–37; 361/302
See application file for complete search history.

(56) References Cited

U.S. PATENT DOCUMENTS

| 2,510,101 | A |   | 6/1950 | Graham |
| 5,291,061 | A | * | 3/1994 | Ball .............................. 257/686 |
| 5,535,097 | A |   | 7/1996 | Ruben et al. |
| 5,905,627 | A | * | 5/1999 | Brendel et al. ................ 361/302 |
| 6,052,623 | A |   | 4/2000 | Fenner et al. |
| 6,376,794 | B1 |  | 4/2002 | Hollar, Jr. |
| 6,402,793 | B1 | * | 6/2002 | Miltich et al. ............... 29/25.03 |
| 6,417,445 | B1 | * | 7/2002 | Sato et al. ........................ 174/36 |
| 6,765,780 | B2 | * | 7/2004 | Brendel et al. ................ 361/302 |
| 7,413,482 | B2 | * | 8/2008 | Ries et al. ..................... 439/736 |
| 2001/0034543 | A1 | * | 10/2001 | Haeg et al. ..................... 607/36 |
| 2002/0052633 | A1 | * | 5/2002 | Prutchi et al. .................. 607/36 |
| 2003/0040780 | A1 | * | 2/2003 | Haeg et al. ..................... 607/36 |
| 2005/0060003 | A1 | * | 3/2005 | Taylor et al. ................... 607/36 |
| 2006/0015150 | A1 | * | 1/2006 | Rusin et al. .................... 607/36 |

* cited by examiner

*Primary Examiner* — Nicole F Lavert

(57) ABSTRACT

An electrical interconnect structure for an implantable medical device includes a feedthrough that has a pin extending therefrom. The pin defines a first end and a middle portion. A bonding surface is formed at the first end of the pin, and the bonding surface has a surface area greater than a cross-sectional area of the pin at its middle portion.

7 Claims, 6 Drawing Sheets

ELECTRICAL INTERCONNECTION STRUCTURES AND METHOD

BACKGROUND OF THE INVENTION

The present invention relates to implantable medical devices. More particularly, the present invention relates to electrical interconnection structures for implantable medical devices.

Electrical feedthroughs provide a conductive path extending between the interior of a hermetically sealed container and a point outside the container. Implantable medical devices may include a connector module for connecting leads to the device. The connector module is electrically connected to circuitry inside a sealed case of the implantable medical device through one or more feedthroughs. Typically, an electronic module assembly (EMA) block is connected also to a feedthrough inside the implantable medical device, opposite the connector module. Wires are then connected to bond pads on the EMA block using conductive solders or brazes to complete the electrical connection across the feedthrough.

BRIEF SUMMARY OF THE INVENTION

The present invention provides a method and structures for making electrical interconnections for implantable medical devices. Arc percussion welding can be used according to the present invention to weld together conductor materials. A connection structure can be formed between a wire and a feedthrough pin having an enlarged head.

DETAILED DESCRIPTION

Figure 1:
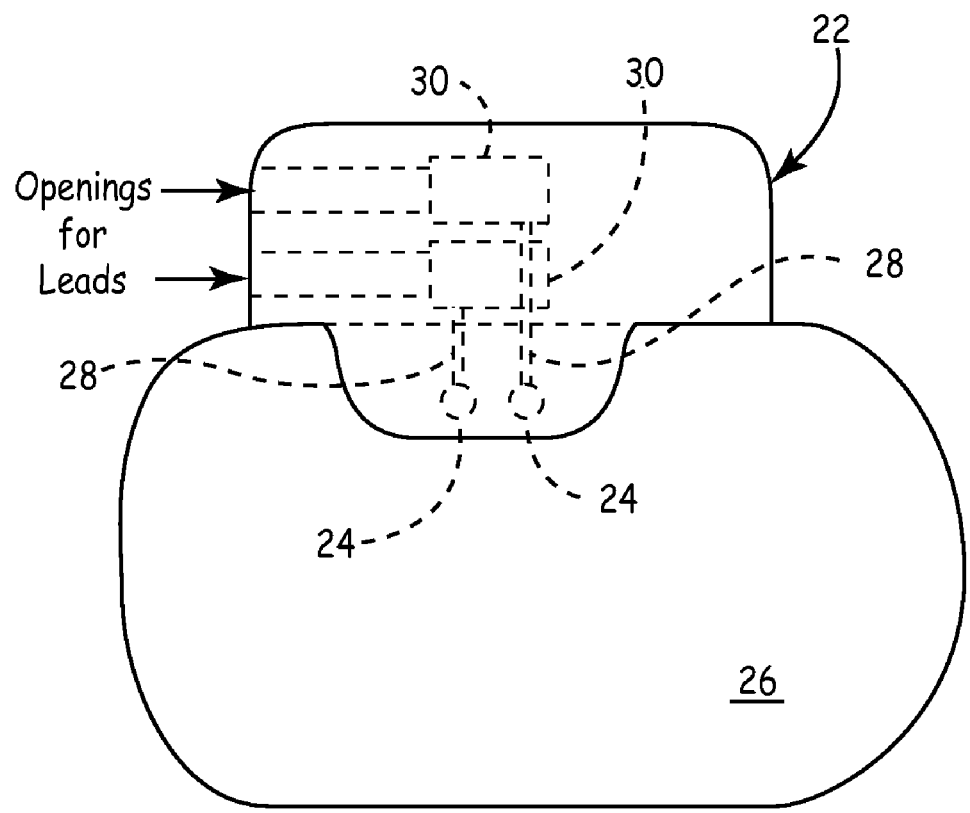
FIG. 1 is a perspective view of an implantable medical device having a connector module that is electrically connected to feedthroughs.

FIG. 1 is a perspective view of an implantable medical device 20 having a connector module 22 (also called a header) that is electrically connected to feedthroughs 24 that pass through a housing or cannister 26 of the device 20. The feedthroughs 24 can be unipolar or multipolar. The connector module 22 includes electrically conductive ribbons 28 that extend between the feedthroughs 24 and components of the connector module 22, such as sleeves or sockets 30 for accepting connector pins of leads (not shown).

Figure 2:
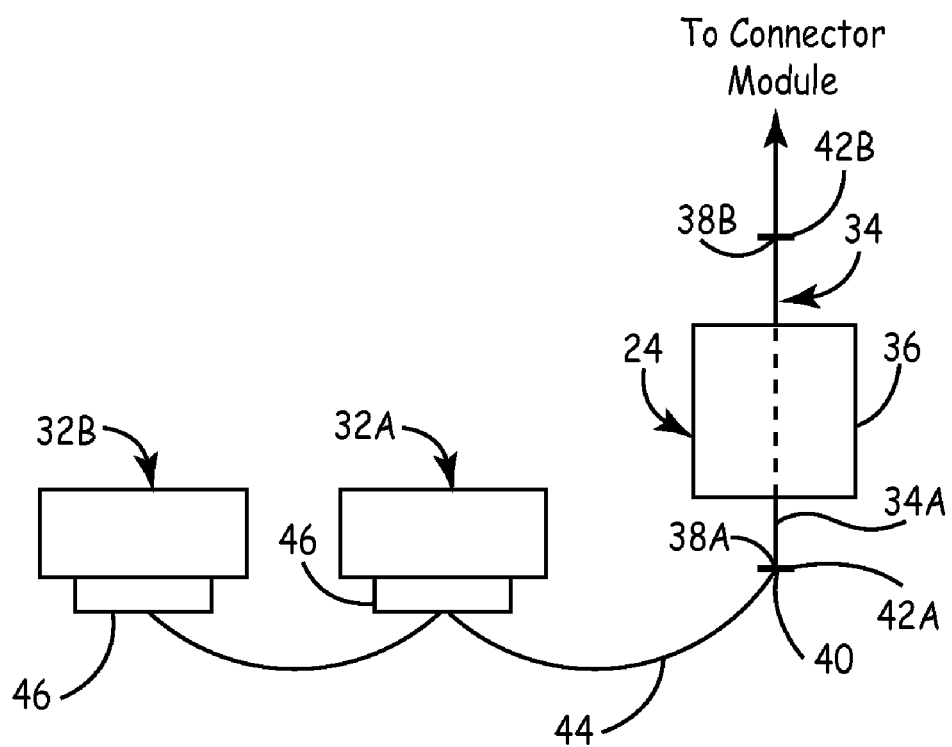
FIG. 2 is a schematic representation of an interconnection assembly between a feedthrough and bond pads.

FIG. 2 is a schematic representation of an interconnection assembly between a feedthrough assembly 24 and bond pads 32A and 32B that are located inside the canister of a device. A feedthrough pin 34 extends through a ferrule 36 of the feedthrough assembly 24. The pin 34 has a first end 38A at an interior side of the ferrule 24A, and a bonding surface 40 is located at an enlarged portion 42A of the first end 38A of the pin 34. A second end 38B of the pin 34 also has a bonding surface 40B on an enlarged portion 42B. The bonding surfaces 40A and 40B provide substantially flat surfaces for making electrical connections. Although FIG. 2 shows enlarged portions 42A and 42B at both ends 38A and 38B of the pin 34, it should be recognized that in further embodiments the pin 34 could have only a single enlarged portion at only one end.

The enlarged portion 42A shown in FIG. 2 can have numerous alternative configurations according to the present invention. For example, the enlarged portion 42A can be formed by welding or otherwise connecting a disc to the first portion of the pin 34. Alternatively, the enlarged portion can be formed by coining the first end 38A of the pin 34. In any configuration, the enlarged portion 42A generally has a greater area than a cross-sectional area of the pin 34 between the enlarged portion 42A and the ferrule 36. The enlarged portion 42A in the illustrated embodiment has a diameter or width of about 30-40 mils. The relatively large surface area provided by the bonding surface 40A of the enlarged portion 42A facilitates aligning and connecting wires and other electrical components to the pin 34. The enlarged portion 42B can be configured similar to enlarged portion 42A.

The bond pads 32A and 32B can be hybrid bond pads of a conventional type known to those skilled in the art of implantable medical device design. The bond pads 32A and 32B can be electrically linked to therapy circuits (not shown) or other components of an implantable medical device, as desired. The particular location of the bond pads 32A and 32B can also vary as desired.

A wire 44 is electrically connected between the pin 34 and the bond pads 32A and 32B. In particular, the wire 44 is electrically connected to the bonding surface 40 and to bonding regions 46 of the bond pads 32A and 32B. The wire 44 can be any electrical conductor in nearly any shape, for example, a conventional ribbon conductor.

The pin 34 and the wire 44 can each be made of a high conductivity material, for example, copper, platinum, tantalum, niobium, palladium, titanium, and alloys thereof. Also, alloys such as MP35N® nickel-cobalt-chromium-molybdenum alloy, nickel- and cobalt-based alloys and stainless steels can be used. Moreover, the wire 44 can be a copper-clad nickel ribbon. It should be recognized that in further embodiments, multiple wires can be connected to the pin 34 as desired.

Figure 3:
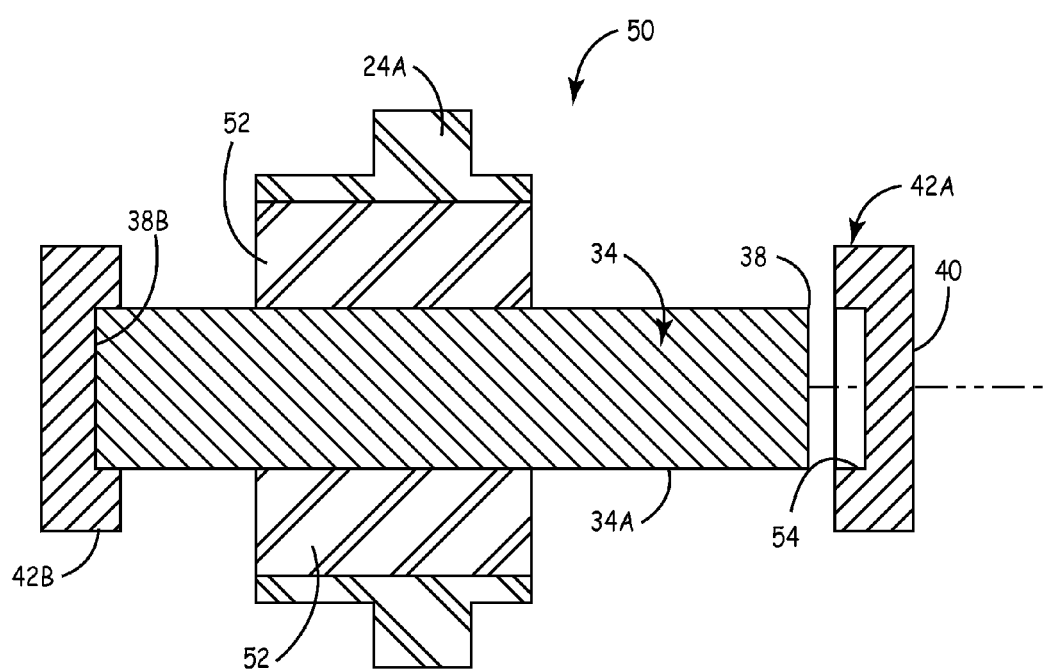
FIG. 3 is an exploded cross-sectional view of a feedthrough assembly.

FIG. 3 is an exploded cross-sectional view of one embodiment of a feedthrough assembly 50 that includes a ferrule 36, a pin 34 extending through the ferrule 36 and a conventional hermetic seal 52 (e.g., a seal made of glass or other non-conductive seal material) between the pin 34 and the ferrule 24A. A disc 42A is positioned at the first end 38A of the pin 34, and for clarity is shown in an exploded cross-sectional manner in FIG. 3. The disc 42A provides a substantially flat bonding surface 40A. The disc 42A can be round, rectangular, or have other shapes, though any shape of the disc 42A generally provides a substantially flat bonding surface 40A.

In the illustrated embodiment, the disc 42A has a recess 54 located opposite the bonding surface 40A. The recess 54 in the disc 42A is configured to mate with the first end 38A of the pin 34, where a welded connection can be made. In further embodiments, the recess 54 can be omitted (see FIG. 7).

Figure 4:
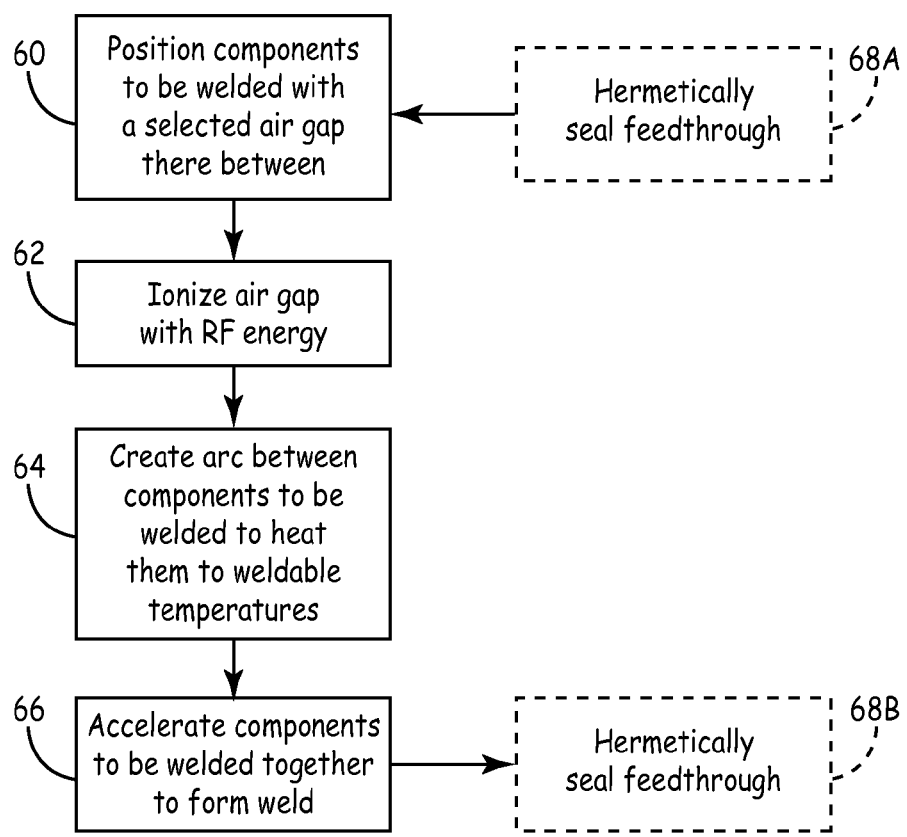
FIG. 4 is a flow chart of a manufacturing process for creating electrical interconnection structures.

FIG. 4 is a flow chart of a manufacturing process for creating electrical interconnection structures according to the present invention. Welded connections between components, such as between a wire and a bonding surface or between a disc and an end of a feedthrough pin, can be made using conventional arc percussion welding equipment.

With arc percussion welding, the components to be welded are first positioned at a selected distance from each other, such that an air gap is formed (step 60). Next, a burst of radio frequency (RF) energy ionizes the air in the air gap (step 62). A suitable cover gas is provided. Then an arc is created between the components to be welded to heat them to weldable temperatures, creating two molten masses (step 64). The arc can be created by discharging capacitor banks of the arc percussion welding equipment. The weldable temperature, and therefore the amount of electrical energy discharged by the capacitor banks, will vary depending on the particular characteristics of components to be welded. Once the components to be welded have reached a weldable temperature, they are accelerated together (step 66). The molten masses combine, metal to metal, are forged together. As the weld cools, a complete alloy bond is formed. One or more electromagnetic actuators can be used to accelerate the components to be welded together.

The arc percussion welding process can be performed to make an electrical connection at a feedthrough, and to form structures as shown and described with respect to FIGS. 1-3. In such situations, the arc percussion welding process can be performed either before or after the feedthrough has been hermetically sealed (alternative steps 68A and 68B). An advantage of the method of forming electrical interconnection structures according to the present invention is that the electrical connections can easily be made after hermetically sealing the feedthrough.

It should be recognized that the method described above can be used in conjunction with conventional techniques for making electrical connections in implantable medical devices. For example, gas tungsten arc welding, electron beam welding, resistance welding, ultrasonic welding, laser welding, friction welding, coining and conductive adhesives can also be used. With respect to the structures shown in FIG. 2, for instance, the electrical connection between the wire 44 and the bonding surface 40 can be formed by one technique and the electrical connection between the wire 44 and the bond pad 32A by another technique.

Figure 5:
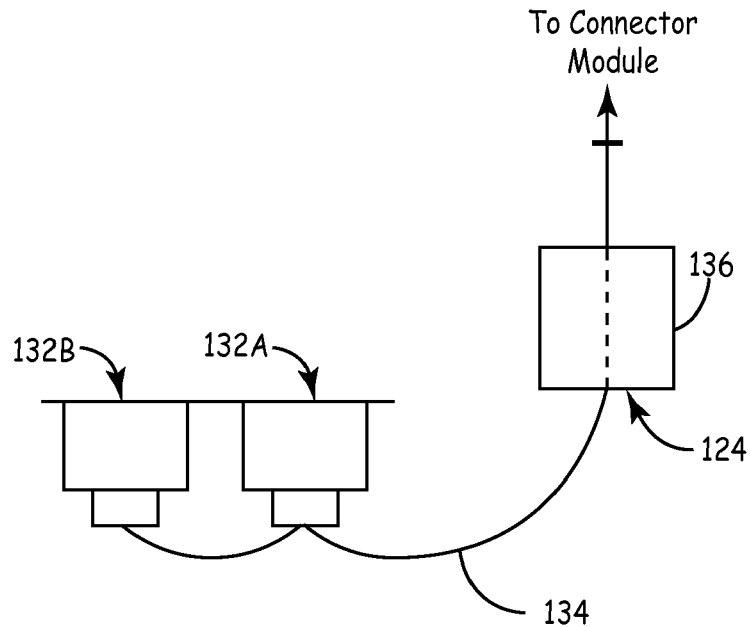
FIG. 5 is a schematic representation of an alternative embodiment of an interconnection assembly.

The structures and method of the present invention can be applied in numerous ways. The following are some examples of alternative embodiments of the present invention. FIG. 5 is a schematic representation of an alternative interconnection assembly that includes a feedthrough assembly 124 and a pair of hybrid bond pads 132A and 132B. A feedthrough pin 134, which extends through ferrule 136, is electrically connected to the hybrid bond pads 132A and 132B directly. In other words, the pin 134 is directly connected to the bond pads 132A and 132B without the need for a separate wire therebetween. The pin 134 can be specially shaped or deflected to properly align it with respect to the bond pad 132A to make the electrical connection therebetween. Moreover, the pin 134 can optionally include an enlarged portion in further embodiments. The connection between the pin 134 and the bond pad 132A can be made using arc percussion welding.

Figure 6:
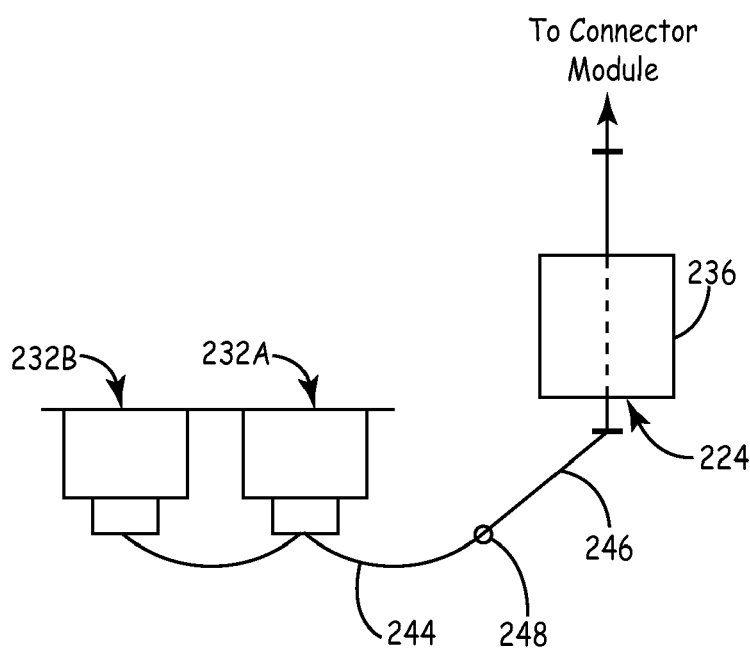
FIG. 6 is a schematic representation of another alternative embodiment of an interconnection assembly.

FIG. 6 is a schematic representation of another alternative embodiment of an interconnection assembly that includes a feedthrough assembly 224 and a pair of hybrid bond pads 232A and 232B. A first wire 224 is connected to the bond pads 232A and 232B. A second wire 246 extends from the feedthrough 224 (e.g., from an enlarged end of a pin 234 that extends through a ferrule 236 of the feedthrough 224), and is connected to the first wire 244 at a joint location 248. The first and second wires 244 and 246, respectively, are connected together in an end-to-end configuration. In this embodiment, the connection between the first and second wires 244 and 246 enables the bond pads 232A and 232B and the feedthrough to be assembled and connected to separate wires (244 and 146) independently and later joined together at the joint location 248. The joint can be formed using arc percussion welding.

Figure 7:
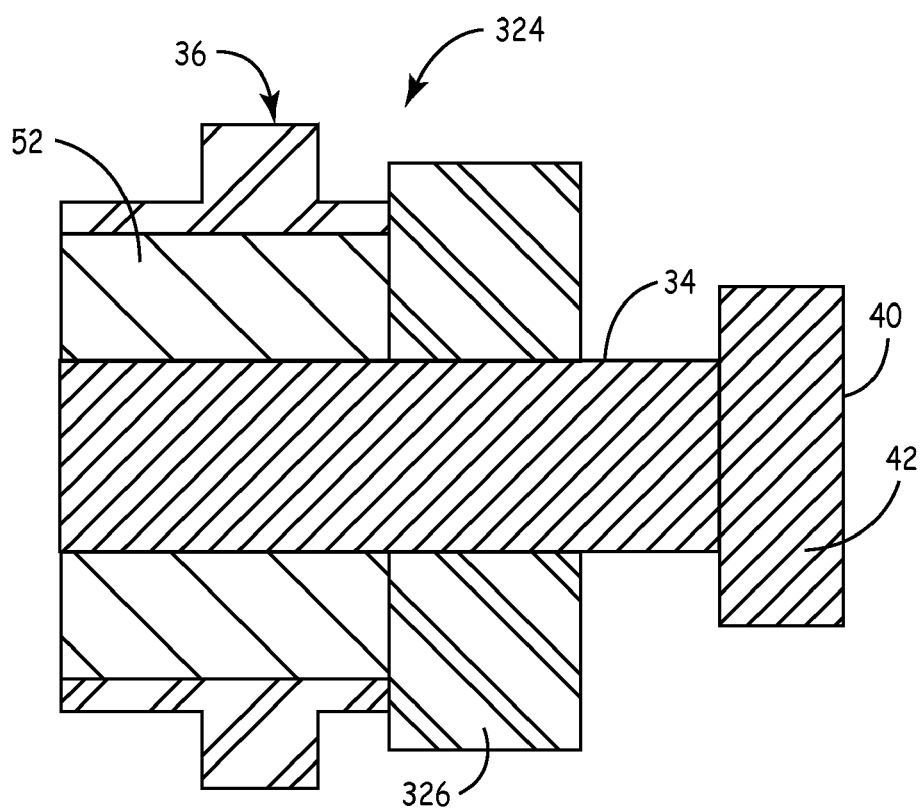
FIG. 7 is a cross-sectional view of a feedthrough assembly with a washer.

FIG. 7 is a schematic representation of a feedthrough assembly 324 that includes a ferrule 36 and a pin 34 with an enlarged portion 42. The feedthrough assembly 324 is generally similar to those described above. However, the feedthrough assembly shown in FIG. 7 further includes a non-conductive washer 326 that is positioned around the pin 34, between the ferrule 36 and the enlarged portion 42 of the pin 34. The washer 326 reduces the risk of welding splatter when the enlarged portion 42 is formed on the pin 34, and can be placed around the pin 34 permanently or temporarily (and removed after the enlarged portion 42 is formed on the pin 34). The particular size and shape of the washer 326 can vary as desired.

The present invention provides for the use of arc percussion welding to weld together conductor materials used in implantable medical devices, and for connection structures to be formed between a wire and a feedthrough pin having an enlarged, nailhead-like head portion. Reliable electrical connections can be easily and simply made between a feedthrough and other components without the need for an electronic module assembly (EMA) block. By omitting the EMA block, manufacturing costs can be reduced and space inside an implantable medical device can be conserved.

Although the present invention has been described with reference to preferred embodiments, workers skilled in the art will recognize that changes may be made in form and detail without departing from the spirit and scope of the invention. For example, the interconnection structures of the present invention can be used with nearly any type of implantable medical device.

The invention claimed is:

1. An electrical interconnect structure for an implantable medical device, the interconnect structure comprising:
    a feedthrough having a pin extending from the feedthrough, the pin structure defining a first end, a second end, and a middle portion, wherein the middle portion of the pin has a first cross-sectional area;
    a bonding surface at the first end of the pin and a bonding surface at the second end of the pin, wherein each bonding surface has a surface area greater than the first cross-sectional area of the pin; and
    a first wire that is electrically connected to the bonding surface and a second wire directly welded to the first wire in an end-to-end configuration.

2. The interconnect structure of claim 1 and further comprising:
    a disc attached to the first end of the pin, wherein the disc defines the bonding surface.

3. The interconnect structure of claim 2, wherein the disc is welded to the first end of the pin.

4. The interconnect structure of claim 2, wherein the disc has a recess defined therein, and wherein a portion of the pin extends into the recess of the disc.

5. The interconnect structure of claim 1 and further comprising:
    a bond pad, wherein the pin has a second end opposite the first end, and wherein the second end of the pin is directly connected to the bond pad to form an electrical connection.

6. The interconnect structure of claim 1 and further comprising:
    a non-conductive washer positioned about the middle portion of the pin.

7. The interconnect structure of claim 1, wherein the bonding surface is defined by a coined portion of the pin.

* * * * *